(12) United States Patent
Silverman

(10) Patent No.: US 11,701,212 B2
(45) Date of Patent: *Jul. 18, 2023

(54) EDENTULOUS SPECIFIC SUPPORT AND AESTHETIC RESTORATIVE APPLIANCE

(71) Applicant: Joshua T. Silverman, Los Angeles, CA (US)

(72) Inventor: Joshua T. Silverman, Los Angeles, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/974,082

(22) Filed: Oct. 26, 2022

(65) Prior Publication Data
US 2023/0049541 A1 Feb. 16, 2023

Related U.S. Application Data

(63) Continuation of application No. 16/359,003, filed on Mar. 20, 2019, now Pat. No. 11,510,767.

(60) Provisional application No. 62/646,045, filed on Mar. 21, 2018.

(51) Int. Cl.
A61F 2/00 (2006.01)
A61C 19/06 (2006.01)

(52) U.S. Cl.
CPC .......... *A61F 2/0059* (2013.01); *A61C 19/063* (2013.01); *A61F 2230/0013* (2013.01)

(58) Field of Classification Search
CPC ................. A61F 2/00; A61C 19/06
See application file for complete search history.

(56) References Cited

PUBLICATIONS

Silverman, "Edentulous Specific Support and Aesthetic Restorative Appliance", U.S. Appl. No. 16/359,003, filed Mar. 20, 2019.

*Primary Examiner* — Matthew W Schall
(74) *Attorney, Agent, or Firm* — Keating and Bennett, LLP

(57) ABSTRACT

An edentulous mouth insert appliance for mounting upon the edentulous gum of a patient, comprises a u-shaped frame formed of a rigid flexible material, with a portion to embrace the gum and a portion extending beyond the gum with an exposed surface to replicate a bite aligned with the corresponding occlusal plane. The frame has a base supporting a pair of inner and outer side walls spaced apart by the base a distance allowing the frame to encircle and cover the edentulous gum with a space between inner surfaces of the frame and the gum. A fill within the frame fills the space between the frame and the gum upon which the appliance is fitted, providing a void-free seal between the apparatus and the gum.

20 Claims, 3 Drawing Sheets

EDENTULOUS SPECIFIC SUPPORT AND AESTHETIC RESTORATIVE APPLIANCE

FIELD OF THE INVENTION

The present invention is directed to a periodontal appliance for an edentulous (teeth-lacking) patient. In particular it is directed to an appliance to interface with a patient's maxilla or mandible fully without teeth being present on the ridge. The appliance is designed to have an outer shape of the mandibular and maxilla structure to which it is attached to provide aesthetic and functional improvement in the edentulous oral cavity and to restore natural facial appearance, basic mechanical functionality, and enhanced oral hygiene applications. The new appliance is not a temporary or permanent replacement for teeth, as an edentulous ridge or oral cavity has a unique anatomical structure and pathology that must be addressed to restore and maintain enhanced general and oral health.

BACKGROUND OF THE INVENTION

An exponential growth of the edentulous population is forecasted to affect 200 million Americans within 15 years; global prosthodontics and medical experts have documented the severity of the issue and conclude existing edentulous hygiene methods and education are not effective. Elderly and immune-suppressed edentulous patients in particular need access to a sterile appliance in order to decrease morbidity and other serious health defects.

Flexible rubber and plastic universal mouthpieces are designed to provide protection for the teeth during contact sports. Medical grade mouthpieces are commonly used to protect the teeth from grinding (bruxism), in addition to providing any number of cosmetic and health related benefits for a dentally correct mouth; all have a primary function of enhancing or interfacing with a set of teeth.

The existing art for mouthpieces and guards with utility only applicable to teeth is extensive; most cannot accommodate braces but all require and function with at least one set of teeth. Improvements of the art include new methods and structures for enhanced shock absorption to prevent injuries to the teeth and mouthpieces to be used in conjunction with processes for teeth whitening and teeth straightening. All of the art shares the commonality that they are intended to improve or protect natural teeth in some form, are typically molded and anchored to the teeth for a custom fit and retention; they all require teeth and are completely incompatible with an edentulous mouth.

The edentulous mouth cannot accommodate the existing art, nor benefit from the intended use for protection or maintenance of mouthpieces common to a user with healthy teeth. The anatomy of an edentulous patient is medically and anatomically unique, requiring specialized and unique dimensions and features designed to meet the parameters and needs of the edentulous user.

For the edentulous patient, conventional dentures provide for a realistic looking prosthetic appliance to replace the teeth, typically comprising at least a hard composite pallet body and realistic acrylic teeth.

There are two primary functions of a removable denture; to provide an aesthetically realistic and functional replacement of the teeth and to allow for mastication of solid foods. It is designed to adhere tightly to the gingivae, typically with an adhesive to create a seal, and allows for typical mastication of solid food. It is considered a prosthetic appliance. While its primary function is to replace and provide realistic teeth, studies have concluded that sealing the gum and depriving it of oxygen can damages the gingivae; healing of the gingivae is not possible without exposure to oxygen.

Edentulous bone and ridges naturally shrink and melt away. The use of conventional dentures has been proven to increase the progression of this chronic issue; eventually the ridge line and especially the mandibular ridge completely reabsorb into the jawbone. Without teeth to stimulate bone growth this deterioration results in a unsightly sunken face, and leaves the edentulous patient permanently disfigured, which seriously impedes quality of life. Both short and long term tissue damage is a negative side effect of extended denture use and is indicative of a greater risk to general health.

A 25-year-long study published in 1972 by Dr. Antje Tallgren of the Royal Dental College in Denmark concluded "denture wearers have continual bone loss; the biting force on the gum tissue irritates the bone and it melts away decreasing in volume and density."

The rate of reduction in size of the residual ridge is maximum in the first three months and then gradually tapers off. The bony remodeling that subsequently takes place occurs in two phases: an initial and fairly rapid phase that can be observed in the first 3 months and the subsequent slow, minimal yet continuous resorption.

During the initial period there is new bone formation with loss of almost all of the alveolar crest height and simultaneous reduction of approximately two-thirds of the ridge width. These changes continue over the initial ten to twelve week periods.

Between six and twelve months, part of the new laid-down bone undergoes further remodeling resulting in the further reduction of the alveolar ridge width until it is reduced to approximately half.

The rate of resorption then slows down to minimal levels and continues throughout life, resulting in loss of varying amounts of jaw structure, finally leaving the patient a 'dental cripple'. This phenomenon is known as Residual Ridge Resorption (RRR). The American Dental Association (ADA) advises patients to remove dentures at bedtime to promote tissue healing and related health issues. The gums cannot breathe through a sealed denture; oxygen is required for healing the gums.

In addition to bone resorption, there are other potentially serious general health issues that can arise due to denture use.

Denture plaque (DP) is defined as a dense microbial layer comprised of microorganisms and their metabolites. It may contain more than 1011 organisms per gram in wet weight and has essentially the same structure as dental plaque on natural teeth. The composition of these microbial flora also resembles that of dental plaque, except for an increased number of *Candida* spp. *Candida* biofilm on dentures leads to a decrease in the bacterial diversity and then to a qualitative change in the composition of the oral microbiota.

DP containing *Candida* can give rise to denture-induced stomatitis, root caries, and periodontitis. In addition, if the oral mucosa is weakened, the friction of the prosthesis can facilitate the breaking of the epithelial barrier and increase the risk of the passage of germs into the bloodstream.

Moreover, the continuous swallowing or respiration of microorganisms from DP exposes patients, particularly the immune compromised host or polymedicated elderly, to the risk of unexpected infections.

Dentures may present a putative risk of infection, especially for patients with lung and digestive diseases. It seems important to prevent this risk by means of information and patient education. Patient awareness of the nature of the risk and its consequences should improve the control of prosthetic biofilm and reduce infection rates. (18)

Other health concerns, including increases in certain oral cancers, increased pneumonia risk for users who wear their dentures during sleep, are associated with denture use.

Accordingly it is a purpose of the present invention to serve as relief appliance for a conventional denture, intended for use on the gingivae. The use of the appliance in tandem with a denture can provide for a significant and immediate reduction in exposure to denture plaque build up and denture adhesives.

A further purpose of the present invention is to provide an alternative to a conventional denture for the edentulous user, providing comfort and periodontal benefit. It is not intended for mastication or to be a realistic replacement of functional teeth.

Yet a further purpose is to provide an oral appliance for the edentulous user that compensates for lost human skeletal face and jaw structure.

BRIEF SUMMARY OF THE INVENTION

The present inventive subject matter comprises an inner mouth support appliance designed to accommodate the anatomically unique structure of an edentulous user. It is worn on top of the gum arch on the mandibular or maxilla ridge and is primarily intended for use by a completely edentulous patient. It provides for an alternate temporary appliance used for comfort, support, and rapid replacement when a denture is unavailable or undesired, and can be used as a remedy for damage and discomfort that may be caused from denture use. The invention has further utility in oral surgery situations, especially needed for the treatment in facial trauma. The appliance is not intended to perform a chewing task or mastication of any form, in contrast to dentures or implants.

The appliance compensates for the negative space caused by lost bone and teeth structure, providing the anatomically correct support necessary used to maintain natural facial appearance and speech, prevents jaw fatigue, and absorbs bone-damaging pressure resulting from bite force.

The new appliance comprises a horseshoe or "U" shaped frame, formed of an appropriate such as a rigid yet flexible anti-microbial hypoallergenic material, such as a plastic, polymer or rubber composition. The substrate may include an extended rigid outer extension that compensates for missing teeth structure and helps maintain speech functionality.

The frame carries a moldable liner which fills the interior of the frame and provides contact and a seal between the frame and the gum.

The frame is constructed to seat directly on the gingivae of the maxilla or mandible arch by use of the liner. The frame conforms and adheres to the shape of the gum arch, maintaining placement and retention. It additionally compensates for structural support, normalized speech, and increased quality of life for the end user.

Mendicants can be infused or applied to the interior of the base and delivered to the gingivae for additional relief and repair.

BRIEF DESCRIPTION OF THE DRAWINGS

A fuller understanding of the present invention will be obtained upon consideration of the following detail description thereof when taken in association with the annexed drawings, wherein.

DETAILED DESCRIPTION OF THE INVENTION

Figure 1:
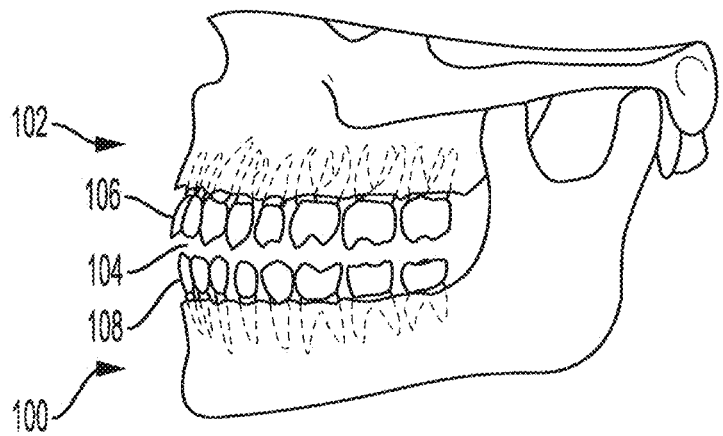
FIG. 1 illustrates a side view of a healthy skeletal dental structure in a side profile.
Figure 2:
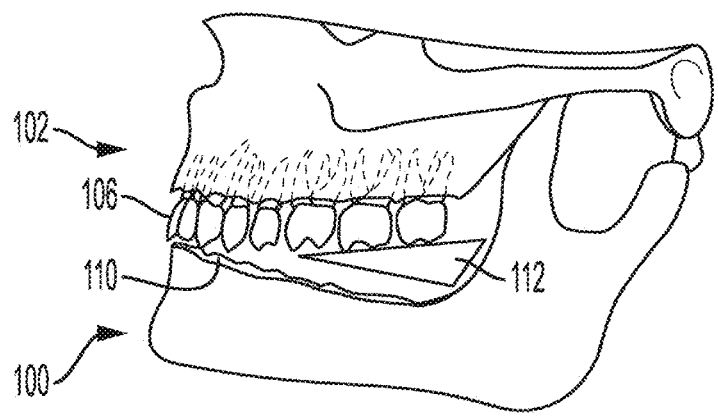
FIG. 2 illustrates an edentulous skeletal side view without any lower teeth present.

FIG. 1 is a side view of a healthy skeletal dental structure. The physiologically correct jaw has normal structural spacing 104 between the mandible 100 and the maxilla 102 when the upper teeth 106 and lower teeth 108 are present. It is to be compared with the jaw orientation depicted in FIG. 2, which illustrates an edentulous skeletal structure with no lower teeth present. When the lower teeth are extracted or missing, the upper teeth 106 naturally impinge upon the lower gum line 110, creating irritation, bone loss, discomfort, and a visible collapsed jaw. The triangle 112 in FIG. 2 represents a negative space, which lacks the presence of the lower teeth. This existence of the space causes discomfort and skeletal muscular tension, as well as outer facial disfigurement. The present invention "recovers" the space and replicates the occlusal platform that disappears in an edentulous individual.

Figure 3:
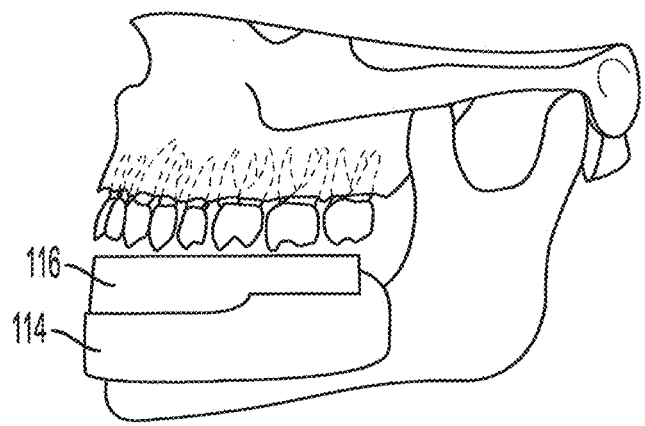
FIG. 3 illustrates the edentulous skeletal structure depicted in FIG. 2 with the appliance of FIG. 3 seated on the lower mandible gum line or ridge side profile.

FIG. 3 presents a simplified side profile diagram of an appliance in accordance with the present invention in a mandibular edentulous mouth. The appliance seats on the lower mandible gum line or ridgeline. With the lower portion 114 of the appliance seated directly on the toothless lower mandible arch of the gum, the extended height of the appliance's upper portion 116 compensates for the missing teeth. With the appliance in place the jaw and skeletal structure is structurally supported. The negative space 112 of FIG. 2 is eliminated and the mandible is returned to its natural position. The jaw's skeletal structure is physiological corrected and supported by the appliance. It is to be understood that a corresponding appliance can be seated on the upper maxillary gum, either in tandem with a mandible-placed appliance or by itself. Thus it is to be understood that the following description illustrating the invention is fully applicable to both mandibular and maxillary embodiments.

Figure 4:
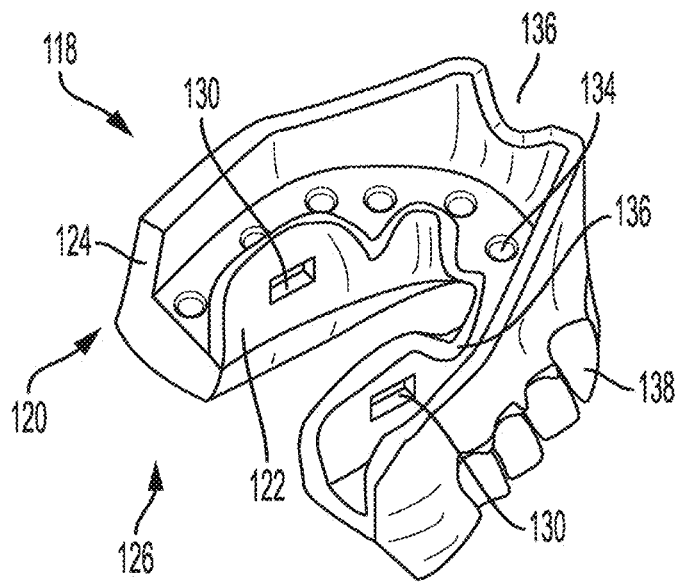
FIG. 4 is a perspective view of a frame for a maxillary embodiment of the invention.

FIG. 4 presents an illustrative construction of the frame of the appliance invention contoured for maxillary mounting. Frame 120 is formed of a generally rigid plastic, polymer or rubber, shaped to fit loosely over the gingiva or alveolar ridge of the maxilla. A similar configuration is used for mandibular fitting. The frame is generally u-shaped in cross-section, forming a channel with inner and outer walls 122, 124 joined by base 126. The frame is preferably dimensioned such that the walls extend rearwardly or proximal in the mouth to location just forward of the position of the first or second molars. However, depending on the specific patent situation, it may alternatively extend over the molar locations. Thus the front-to-back length of the frame is typically on the order of 25-50 mm, while the wall thickness is typically in the range of 1-2 mm. The frame is flexible, and requires only a loose fit over the gingiva. Accordingly, it is possible for there to be a "one size fits all" construction. Alternatively, frames can be stocked in a small number of sizes. The overall front-to back length of a stock frame can be easily shortened or otherwise further adjusted to the patient by trimming. Further, when faced with a particular patient situation, an individualized frame may be formed by a suitable molding process as known in the art, based on an impression of the gingiva on which it is to be mounted. Typically the frame may be manufactured by a thermoforming or injection molding. The frame's channel may be narrowed towards the anterior to conform to the normal narrowing of the gingiva. Typically the rear or proximal end of the channel has a width of 15-30 mm. In this embodiment the frame is of a unitary construction, and comprises a first (upper) portion corresponding to portion 114 in FIG. 3 that fits around the gingiva or alveolar ridge and a second (lower) portion corresponding to portion 116 in FIG. 3 that replicates the occlusal platform lost by the removal of the teeth.

The exterior surface of the lower portion may be molded or incised to simulate the appearance of teeth, and thus may be colored or tinted to replicate the color of teeth. Appropriate portions of the exterior surface of the upper portion may likewise be tinted to replicate the color of the gingiva.

Figure 5:
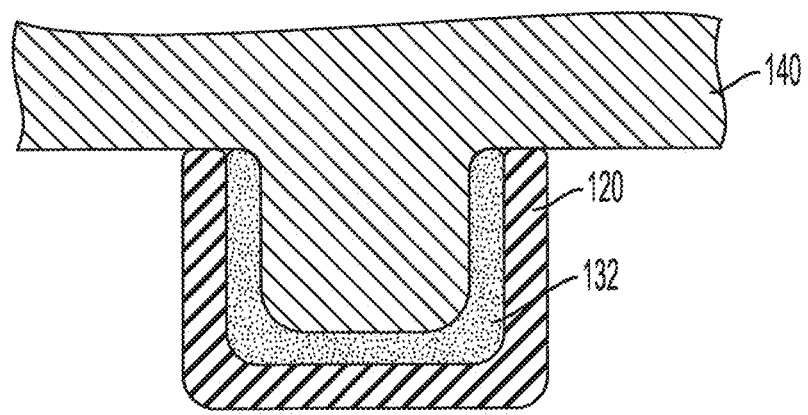
FIG. 5 is a generalized sectional view depicting an appliance in place in a patient's mouth.

As depicted in FIG. 5, fitting of the frame to the gingiva is accomplished by the presence of a fill 132 of a suitable pliable material. The fill is preferably a moldable, biocompatible, self-curing compound, such as polyvinyl siloxane (PVS) as known in the art, typically used for dental impressions. Cellulose gum and polyethylene glycol may also be considered as a fill or lining material. PVS is a putty or dough-like addition-reaction silicone elastomer material, comprising a base and a catalyst provided in separate containers. When the base and catalyst are combined, the curing mechanism in the base is activated. The putty hardens and becomes rigid following a 2 to 5 minutes curing time.

The compound is placed within the frame in the uncured state, and cures and molds to the precise contours of the wearer's gingiva 140 when the appliance is initially placed in position and held to cure. Because the frame has some degree of flexure, it can be held in the proper position with respect to the gingiva as the fill layer cures. The cured layer retains the molded shape and thus insures a precise fit upon subsequent insertion of the appliance.

The fill material may contain medication-dispensing functionality including anti-inflammatory, antibiotic, and/or numbing agents such as benzocaine. Depending on the specific formulation of the fill material, the medication may be incorporated directly into the material or may be provided in a film form or in pockets or cavities incised into the fill after cure.

After the PVS or other fill material is activated, it is placed along the floor and inner side walls of the frame. The appliance is then placed on the corresponding upper or lower gingival ridge. The user bites down against the opposing ridge of teeth, if present, or positive pressure is applied by the installer to position the appliance in its proper position. Due to the flexibility of the frame, it can be pinched to provide better conformance to the gum upon which it is being mounted.

As depicted in FIG. 4, a cutout portion or depression 136 may be provided on the interior wall of the anterior portion of the frame that surrounds the gingiva to enhance adhesion between the fill and the frame. Excess fill flow can exit through the cutout and be excised after cure to provide a smooth frame exterior. Alternatively, as portion of the exited fill may be retained. The mouth-contacting surface of the exited fill may by initially shaped to the contours of the mouth by the wearer's tongue, and subsequently trimmed upon cure. In the maxillary version in particular the exterior flow can be contoured while pliable to rest upon the palate, which may enhance comfort and fit for the appliance.

In addition to the depression 136, the frame may be provided with depressions or apertures 134 in the frame's base 126 to enhance bonding of the fill to the base. Likewise, fill-bonding depressions or apertures 130 in the frame's inner wall may be provided. Excess fill extending beyond the outer surfaces of the frame can be removed after cure.

Once the fill is cured, the impression of the user's gingival ridge and surrounding area become permanent. The rigidity of the cured fill now locks the previously flexible frame into a static width conforming to the individual contours of the gingival ridge upon which it is applied.

The height of the frame, in conjunction with the degree of fill 132 are chosen such that, with the appliance in place on the gum, the plane of the base is aligned with the corresponding occlusal plane as illustrated in FIG. 3, which is an imaginary curved plane formed by the incisal edges of the (missing) anterior teeth and the occlusal surfaces of the posterior teeth. This orientation mimics a proper anatomical bite registration and provides both an attractive appearance and a normal mouth feel for the user. Typical heights for the fill 132 range between 18 and 22 mm, corresponding to a fill volume of about 5-15 ml.

As stated above, similar constructions are utilized for both mandibular and maxillary constructions. For maxillary use the overall width of the appliance ranges from about 25 to 50 mm, corresponding to the size of the wearer's jaw, while mandibular constructions may have an overall width of between 25 and 55 mm.

Figure 6:
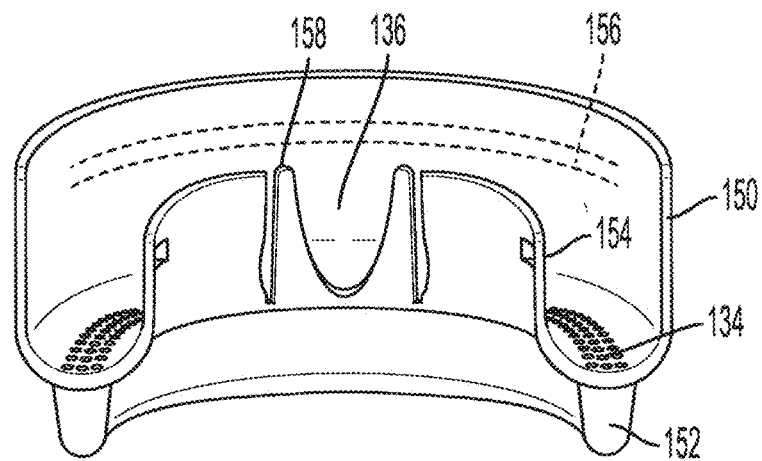
FIG. 6 is a perspective posterior view of an alternative embodiment of the invention.
Figure 7:
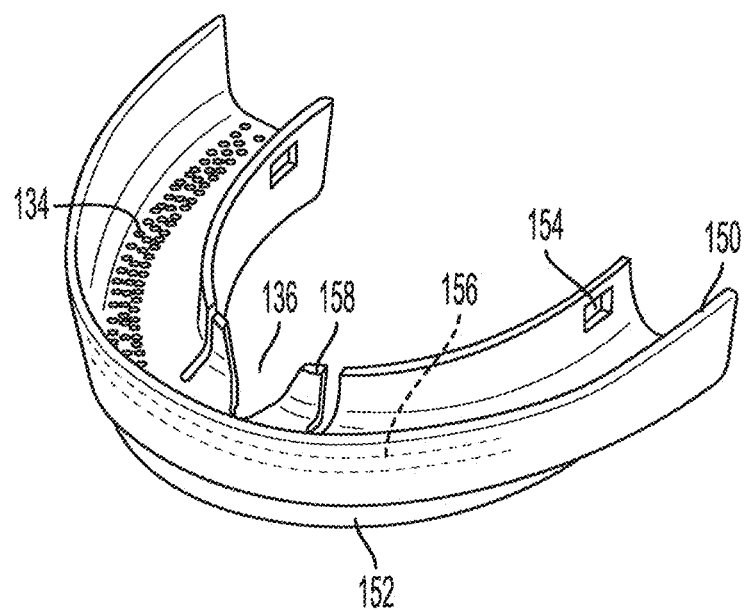
FIG. 7 is a further perspective view of the alternative embodiment.

FIGS. 6 and 7 depict an alternative embodiment for the invention. In this embodiment the tooth-replicating portion may be a solid structure, such that the cavity 156 into which the fill placed is formed only in portion 150. In such a case the amount of fill needed will be lessened. The gum-overlying portion 150 and tooth-replicating portion 152 may be individually cast, typically in an overmolding process as known in the art. Alternatively, a single cast may be used, or the two portions individually cast and subsequently bonded together. As shown, the tooth-replicating portion 152 is shown with a width substantially less than that of the gum-overlying portion. The width ratio is a variable that can take into account the size and geometry of the mouth as well as the desired appearance and aesthetic effect. Use of a two part construction may facilitate the coloring of the portions, whereby the gum—overlying portion material can be dyed an appropriate pink color, while the teeth-overlying portion can be of an appropriate white, off-white or ivory color. The illustrated construction should not be construed as preventing such an embodiment from having both portions 150 and 152 from having identical widths, as shown in FIG. 4 of the first embodiment.

Inner wall 154 of gum-overlying portion 150 retains the a central cutout 1136 to provide an outlet for excess fill material, while adjacent slots 158 improve the flexibility of the appliance for proper fitting on the gum. As an alternative to the generally larger bores as shown in the first embodiment, the fill-bonding bores 134 in the present embodiment may be more numerous and significantly smaller. The purpose remains the same, however; to provide a bonding mechanism between the fill and frame.

FIG. 6 further depicts in phantom the inclusion of insert 160 imbedded or otherwise cast into the outer wall of frame portion 150. Typically in the form of a stainless steel wire as known in the dental arts, the insert provides allows the appliance to be gently bent into a desired arch configuration and retained there by the insert's rigidity. The inclusion of the insert may facilitate the fitting of the appliance to the gingiva during fill cure.

The insert can extend about the entre frame periphery, and be located on either (or both) of the frame walls, or may extend over one or more portions of the wall(s). Alternatively, a thin metal strip may be incorporated. In either event, the insert is chosen to be flexible but with sufficient rigidity to maintain an orientation after being bent.

While the appliance of the present invention is primarily intended for fitting by a medical or dental professional, both as an emergency replacement as well as in connection with oral surgery or for permanent use for an edentulous patient. It can also be offered as a kit to a consumer, preferably for one-time use as an emergency replacement for a lost or damaged denture, and be provided as an unfilled frame and a quantity of PVS or other fill material with instructions for filling the frame and molding it to the gingiva. A supplied fill volume of about 25 ml is typically sufficient.

What is claimed is:

1. An edentulous mouth insert appliance for mounting upon a fully edentulous gum of a patient, the edentulous mouth insert appliance comprising:
   a frame including a base and a pair of inner and outer side walls spaced apart by the base to allow the frame to cover the fully edentulous gum with a space between inner surfaces of the frame and the gum; wherein
   the frame is structured to receive and hold a curable material in the space between the frame and the gum to provide a seal between the edentulous mouth insert appliance and the gum.

2. The edentulous mouth insert appliance according to claim 1, wherein the frame is structured to receive the curable material to position the appliance on the gum such that an outer surface of the base is oriented at a level corresponding to a gingival margin of the gum with an outer surface of the base aligned with a corresponding occlusal plane.

3. The edentulous mouth insert appliance according to claim 1, wherein portions of outer surfaces of the outer side walls are incised to replicate the appearance of teeth.

4. The edentulous mouth insert appliance according to claim 3, wherein portions of the outer surfaces of the outer side walls are colored to replicate the appearance of at least one of teeth or natural gums.

5. The edentulous mouth insert appliance according to claim 1, wherein the frame incudes at least one of an aperture or a cutout portion.

6. The edentulous mouth insert appliance according to claim 1, wherein the frame is formed from a material selected from a group consisting of plastic, composite, and rubber medical grade materials.

7. The edentulous mouth insert appliance according to claim 1, further comprising a medicament associated with the curable material for release when the appliance is worn.

8. The edentulous mouth insert appliance according to claim 7, wherein the medicament is incorporated into the curable material.

9. The edentulous mouth insert appliance according to claim 1, wherein the frame includes a securance structure to secure the curable material to the frame.

10. The edentulous mouth insert appliance according to claim 9, wherein the securance structure includes at least one of an aperture or a bore in the frame.

11. The edentulous mouth insert appliance according to claim 1, wherein the frame includes an insert to facilitate retaining the frame in a desired flexed orientation.

12. The edentulous mouth insert appliance according to claim 11, wherein the insert includes a wire embedded in the frame.

13. The edentulous mouth insert appliance according to claim 1, wherein a thickness of each of the base and the inner and outer walls of the frame is in a range of 1 mm to 2 mm.

14. The edentulous mouth insert appliance according to claim 1, wherein the frame includes a portion that projects upwardly from the base a distance such that, with the curable material positioning the appliance on the gum in alignment with a gingival margin of the gum, a top surface of the portion is aligned with a corresponding occlusal plane.

15. A kit for an edentulous mouth insert appliance for mounting upon a fully edentulous gum of a patient, the kit comprising:
   a frame including a base and a pair of inner and outer side walls spaced apart by the base to allow the frame to cover the fully edentulous gum with a space between inner surfaces of the frame and the gum; and
   a curable material, to be placed within the frame to be located between the frame and the gum to provide a seal between the edentulous mouth insert appliance and the gum.

16. The kit according to claim 15, wherein
   the curable material includes a base and a catalyst; and
   when the base and the catalyst are combined, a curing mechanism in the curable material is activated such that the curable material hardens following a curing time.

17. The kit according to claim 15, wherein the curable material is to be placed within the frame in an uncured state and provides the seal between the edentulous mouth insert appliance and the gum when the curable material has cured.

18. The kit according to claim 15, wherein when the curable material provides the seal between the edentulous mouth insert appliance and the gum, the curable material positions the appliance on the gum such that an outer surface of the base is oriented at a level corresponding to a gingival margin of the gum with an outer surface of the base aligned with a corresponding occlusal plane.

19. The kit according to claim 15, wherein
   the frame includes a portion that projects upwardly from the base; and
   when the curable material provides the seal between the edentulous mouth insert appliance and the gum, a top surface of the portion of the frame is aligned with a corresponding occlusal plane.

20. The kit according to claim 15, wherein the frame includes at least one of an aperture or a bore to secure the curable material to the frame.

* * * * *